(12) United States Patent
Yang et al.

(10) Patent No.: US 12,194,446 B2
(45) Date of Patent: Jan. 14, 2025

(54) SCM-34 MOLECULAR SIEVE, PREPARATION METHOD THEREFOR AND USE THEREOF

(71) Applicants: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

(72) Inventors: Weimin Yang, Shanghai (CN); Jian Qiao, Shanghai (CN); Zhiqing Yuan, Shanghai (CN); Zhendong Wang, Shanghai (CN); Jiawei Teng, Shanghai (CN); Weichuan Tao, Shanghai (CN); Wenhua Fu, Shanghai (CN); Songlin Liu, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

( * ) Notice: Subject to any disclaimer, the term of this patent is extended or adjusted under 35 U.S.C. 154(b) by 85 days.

(21) Appl. No.: 18/245,202

(22) PCT Filed: Sep. 9, 2021

(86) PCT No.: PCT/CN2021/117344
§ 371 (c)(1),
(2) Date: Mar. 14, 2023

(87) PCT Pub. No.: WO2022/052967
PCT Pub. Date: Mar. 17, 2022

(65) Prior Publication Data
US 2023/0356201 A1    Nov. 9, 2023

(30) Foreign Application Priority Data

Sep. 14, 2020 (CN) .......................... 202010962076.8
Apr. 22, 2021 (CN) .......................... 202110438110.6
Jun. 23, 2021 (CN) .......................... 202110699686.8

(51) Int. Cl.
*B01J 29/85* (2006.01)
*B01J 37/00* (2006.01)
(Continued)

(52) U.S. Cl.
CPC ........... *B01J 29/85* (2013.01); *B01J 37/0018* (2013.01); *B01J 37/031* (2013.01); *B01J 37/04* (2013.01);
(Continued)

(58) Field of Classification Search
CPC ...... B01J 29/85; B01J 37/0018; B01J 37/031; B01J 37/04; B01J 2235/15; B01J 2235/30;
(Continued)

(56) References Cited

U.S. PATENT DOCUMENTS 4,310,440 A   1/1982 Wilson et al.
4,499,327 A * 2/1985 Kaiser ................ C01B 37/08
                                                  423/305
(Continued)

FOREIGN PATENT DOCUMENTS

CN   1363517 A   8/2002
CN   1388062 A   1/2003
(Continued)

OTHER PUBLICATIONS

Zhong, Shenglai et al.; "Fast preparation of ERI-structure ALPO-17 and SAPO-17 in the presences of isomorphous and heterogeneous seeds"; Microporous and Mesoporous Materials, Elsevier, Amsterdam, NL; vol. 263; Year: 2018; ISSN: 1387-1811; pp. 11-20.
(Continued)

*Primary Examiner* — In Suk C Bullock
*Assistant Examiner* — Jason Y Chong
(74) *Attorney, Agent, or Firm* — NKL Law; Allen Xue (57) ABSTRACT

A SCM-34 molecular sieve, preparation method therefor and use thereof are provided. The SCM-34 molecular sieve contains aluminum, phosphorus, oxygen and optionally silicon. In the XRD diffraction data of the molecular sieve, a 2θ
(Continued)

degree of the strongest peak within the range of 5-50° is 7.59±0.2. The SCM-34 molecular sieve has a new skeleton structure and can be used to prepare a metal-containing AFI type molecular sieve or an SAPO-17 molecular sieve.

13 Claims, 5 Drawing Sheets

(51) Int. Cl.
| | | |
|---|---|---|
| *B01J 37/03* | (2006.01) | |
| *B01J 37/04* | (2006.01) | |
| *C01B 39/54* | (2006.01) | |
| *C07C 1/04* | (2006.01) | |
| *C07C 1/20* | (2006.01) | |
| *C07C 1/247* | (2006.01) | |

(52) U.S. Cl.
CPC ............ *C01B 39/54* (2013.01); *C07C 1/043* (2013.01); *C07C 1/247* (2013.01); *C01P 2002/72* (2013.01); *C01P 2002/74* (2013.01); *C01P 2002/88* (2013.01); *C01P 2004/03* (2013.01)

(58) Field of Classification Search
CPC ....... C01B 39/026; C01B 39/54; C01B 37/04; C01B 37/08; C07C 1/043; C07C 1/247; C01P 2002/72; C01P 2002/74; C01P 2002/88; C01P 2004/03; C10G 2/334
See application file for complete search history.

(56) References Cited

U.S. PATENT DOCUMENTS

| | | |
|---|---|---|
| 10,336,622 B1 | 7/2019 | Yuhas et al. |
| 2004/0116282 A1 | 6/2004 | Mees et al. |
| 2010/0196261 A1 | 8/2010 | Pai et al. |
| 2011/0295050 A1 | 12/2011 | Nesterenko et al. |

FOREIGN PATENT DOCUMENTS

| | | |
|---|---|---|
| CN | 101121522 A | 2/2008 |
| CN | 101397143 A | 4/2009 |
| CN | 103922361 A | 7/2014 |
| CN | 103964457 A | 8/2014 |
| CN | 104340985 A | 2/2015 |
| CN | 104437615 A | 3/2015 |
| CN | 106241830 A | 12/2016 |
| CN | 106629760 A | 5/2017 |
| CN | 107032363 A | 8/2017 |
| CN | 107511175 A | 12/2017 |
| CN | 109081360 A | 12/2018 |
| CN | 111099603 A | 5/2020 |
| CN | 111099612 A | 5/2020 |
| CN | 111099625 A | 5/2020 |
| CN | 112520751 A | 3/2021 |
| CN | 112520756 A | 3/2021 |
| CN | 115991482 A | 4/2023 |
| IN | 109422272 A | 3/2019 |
| RU | 2203875 C2 | 5/2003 |
| WO | 03040037 A1 | 5/2003 |
| WO | 2016090612 A1 | 6/2016 |

OTHER PUBLICATIONS

Lischke, G. et al.; "Acidity and catalytic properties of MeAPO-5 molecular sieves"; Applied Catalysis A: General, Elsevier, Amsterdam, NL; vol. 166, No. 2; Year: 1998; ISSN. 0926-860X; pp. 351-361.

Bushuev Yu.G.; "Zeolites. Computer Modeling of Zeolite Materials"; Ivanovo, Ivanovo State Chemical-Technological University, Year: 2011, pp. 18-19.

Byrappa K. et al.; "Handbook of Hydrothermal Technolog—A Technology for Crystal Growth and Materials Processing"; Noyes Publications/William Andrew Publishing LLC., Year: 2001, ISBN: 0-8155-1445-X, pp. 335.

Tagiev, D.B. et al.; "Catalytic properties of zeolites in oxidation reactions"; Advances in Chemistry, Science, Year: 1981, vol. L, Issue 11, pp. 1929-1959.

* cited by examiner

SCM-34 MOLECULAR SIEVE, PREPARATION METHOD THEREFOR AND USE THEREOF

TECHNICAL FIELD

The present invention pertains to the field of molecular sieve, in particular to a SCM-34 molecular sieve, and preparation method therefor and use thereof.

BACKGROUND ART

Porous materials are a kind of solid compounds with regular pore structures. According to the definition of the International Union of Pure and Applied Chemistry (IUPAC), porous materials with pore diameters of less than 2 nm are classified as micropore materials; porous materials with pore diameters of more than 2 nm are classified as mesopore materials or macropore materials (with pore diameters of more than 50 nm). Molecular sieve materials generally have pore channel diameters of less than 2 nm, belong to micropore materials and are a kind of porous materials mainly characterized by selective adsorption. Their unique pore channel system renders them capable of sieving small molecules with different sizes, where the name of "molecular sieve" comes. Moreover, these materials have a wide range of inner pore cavity sizes and have rich and diverse topology structures, have been widely used in fields such as adsorption separation, heterogeneous catalysis, carrier of various guest molecules and ion exchange, and have achieved excellent technical results.

Traditional zeolite molecular sieves are a kind of crystalline silicate materials, are generally formed by connecting silicon-oxygen tetrahedron $[SiO_4]^{4-}$ and aluminum-oxygen tetrahedron $[AlO_4]^{5-}$ via shared oxygen atoms, and are generally referred to as $TO_4$ tetrahedron (a primary structural unit), wherein the silicon element can also be subjected to a partial isomorphous substitution by other elements, in particular some trivalent or tetravalent elements such as Al, B, Ga, Ge, Ti, etc. Owning to some particularities of their structures and chemical properties, zeolite molecular sieves are widely used in catalysis, adsorption, ion exchange and other fields. A key factor deciding the application performance of molecular sieves is the characteristics of their pore channels or cages, which are in turn determined by the intrinsic crystal structure of molecular sieves. Therefore, to obtain a molecular sieve with a new crystal structure is of great significance for exploiting the application of molecular sieves.

In 1982, scientists, named S. T. Wilson and E. M. Flanigen etc. of Union Carbide Corp. (UCC) of USA, by employing aluminum sources, phosphorus sources and organic templates, successfully synthesized and developed a brand new family of molecular sieves: aluminophosphate molecular sieves $AlPO_{4-n}$ with n representing model number (U.S. Pat. No. 4,310,440). After two years, on the basis of $AlPO_{4-n}$, by partially replacing Al atoms and P atoms in AlPO skeleton with Si atoms, UCC successfully prepared another series of silicoaluminophosphate molecular sieves: SAPO-n, where n represents model number. After replacing P or Al atoms of the original AlPO framework with Si atoms, a non-neutral skeleton composed of $SiO_4$, $AlO_4$ and $PO_4$ tetrahedrons is formed in the structure of SAPO-n. In the skeleton of this type of molecular sieves, silicon is present in two ways: (1) replacing one P atom with one Si atom; (2) replacing a pair of aluminum atom and phosphorus atom respectively with two silicon atoms. The representative SAPO-n molecular sieve is an SAPO-34 molecular sieve with a topological structure of CHA. The molecular sieve has a skeleton structure similar to chabasite and belongs to cubic system. The structural motif is composed of $AlO_2^-$, $SiO_2$ and $PO_2^+$ tetrahedrons. The skeleton contains an ellipsoidal supercage and a three-dimensional cross structure with 8-membered ring pore channel. The 8-membered ring pore channel has a pore diameter of about 0.38 nm. The supercage has a pore opening diameter maintained between 0.43 and 0.50 nm. Due to its suitable proton acidity, larger specific surface area, better adsorption performance, better thermal stability, good hydrothermal stability and excellent shape selectivity of pore channel structure to light olefins, SAPO-34 molecular sieve has been successfully commercialized as the catalyst for methanol to light olefins (MTO), and has shown very good catalytic activity and selectivity.

At present, molecular sieves with known topological structures are mostly prepared by hydrothermal or solvothermal synthesis. The major steps of a typical hydrothermal or solvothermal synthesis method are: firstly evenly mixing reactants such as the metallic source, the non-metallic source, the organic template and the solvent etc. to obtain an initial sol, i.e., a mixture to be crystallized, and then placing the mixture to be crystallized in a reactor with PTFE as the lining and a stainless steel as the outer wall for a crystallization reaction under a certain temperature and an autogenous pressure after sealing, just like the process of rock formation in the earth, i.e. a process of precipitation of a molecular sieve crystal from a crystallization mixture. Specifically, taking the synthesis of silicoaluminophosphate SAPO-34 molecular sieves as an example, the reaction mixture includes skeleton reactants (such as silica sol, phosphoric acid and aluminum oxide), the structure directing agent (SDA) and water, which are uniformly mixed, and is placed in an oven at a fixed temperature (160-220° C.) for several days in a static or dynamic manner for crystallization reaction. When the crystallization reaction is completed, a solid product containing SAPO-34 molecular sieve is filtered out and dried for the later use.

Up to now (Aug. 4, 2021), according to the International Zeolite Association, including the latest AlPO-91 molecular sieve with a topological structure of ANO [U.S. Pat. No. 10,336,622 B1, (2019), Crystalline metallophosphates, their method of preparation, and use, Yuhas, B. D., Wilson, K. N., Sylejmani-Rekaliu, M., Mowat, J. P. S., Sinkler, W.], there are 255 molecular sieves with different topological structures in total. Although many different crystalline molecular sieves have been obtained, developing novel molecular sieves with desirable properties for gas separation and drying, hydrocarbon conversion reactions and other applications is still a hotspot of the current research.

Contents of the Invention

The present invention provides a SCM-34 molecular sieve(, and a preparation method therefor and a use thereof. The SCM-34 molecular sieve is a novel molecular sieve with a new skeleton structure and can be used to prepare a metal-containing AFI type molecular sieve or an SAPO-17 molecular sieve, meeting the different needs for catalysts in the chemical production.

According to the first aspect of the present invention, a SCM-34 molecular sieve is provided, characterized in that the SCM-34 molecular sieve comprises aluminum, phosphorus, oxygen and optionally silicon; in XRD diffraction data of the molecular sieve, a 2θ degree of the strongest peak within the range of 5-50° is 7.59±0.2; an X-ray diffraction pattern of the SCM-34 molecular sieve includes X-ray diffraction peaks shown in the following table:

| 2θ (°) | relative intensity, [(I/I$_0$) × 100] |
|---|---|
| 7.59 ± 0.2 | 100 |
| 10.81 ± 0.1 | 5-50 |
| 16.52 ± 0.1 | 5-50 |
| 17.97 ± 0.1 | 5-50 |
| 23.34 ± 0.05 | 5-50 |

The present invention further provides a SCM-34 molecular sieve. The SCM-34 molecular sieve has a schematic chemical composition as shown in the formula "Al$_2$O$_3$: xSiO$_2$: yP$_2$O", wherein 0≤x≤0.5, 0.75≤y≤1.5; in the XRD diffraction data of the molecular sieve, the 2θ degree of the strongest peak within the range of 5-50° is 7.59±0.2; the X-ray diffraction pattern of the SCM-34 molecular sieve includes X-ray diffraction peaks shown in the following table:

| 2θ (°) | relative intensity, [(I/I$_0$) × 100] |
|---|---|
| 7.59 ± 0.2 | 100 |
| 10.81 ± 0.1 | 5-50 |
| 16.52 ± 0.1 | 5-50 |
| 17.97 ± 0.1 | 5-50 |
| 23.34 ± 0.05 | 5-50 |
| 34.74 ± 0.05 | 5-50 |

Furthermore, the X-ray diffraction pattern of the SCM-34 molecular sieve also includes the X-ray diffraction peaks shown in the following table:

| 2θ (°) | relative intensity, [(I/I$_0$) × 100] |
|---|---|
| 14.25 ± 0.1 | 5-50 |
| 21.01 ± 0.1 | 10-20 |
| 24.27 ± 0.05 | 5-50 |
| 26.05 ± 0.05 | 5-50 |
| 27.82 ± 0.05 | 5-50 |
| 28.15 ± 0.02 | 5-50 |
| 30.03 ± 0.02 | 5-50 |

Furthermore, the X-ray diffraction pattern of the SCM-34 molecular sieve also includes the X-ray diffraction peaks shown in the following table:

| 2θ (°) | relative intensity, [(I/I$_0$) × 100] |
|---|---|
| 10.33 ± 0.1 | 10-20 |
| 12.09 ± 0.1 | 5-50 |
| 19.77 ± 0.1 | 5-50 |
| 31.33 ± 0.01 | 5-50 |
| 38.29 ± 0.01 | 5-50 |

Therein, the incident ray of the X-ray diffraction is CuKα1.

According to the second aspect of the present invention, a method of preparing the aforementioned SCM-34 molecular sieve is provided, comprising: crystallizing a mixture containing an aluminum source, a phosphorus source, an organic template R1 and an organic template R2, a solvent S1, a solvent S2 and a solvent S3, and optionally a silicon source to obtain a SCM-34 molecular sieve;

wherein, the organic template R1 is selected from one or more of quaternary ammonium salts and/or quaternary ammonium bases; the organic template R2 is selected from one or more of imidazole, pyrrolidine, and derivatives thereof; the solvent S1 is selected from one or more of amide group solvents; the solvent S2 is selected from one or more of the cyclic organic solvents; the solvent S3 is selected from one or more of water or lower alcohols, wherein the organic template R1 and organic template R2 represent different organic templates from each other, and the solvent S1, the solvent S2 and the solvent S3 represent different solvents from each other.

Further, the organic template R1 is selected from one or more of tetraethylammonium bromide, tetraethylammonium hydroxide, tetrapropylammonium bromide, tetrapropylammonium hydroxide, tetrabutylammonium bromide, tetrabutylammonium hydroxide; the organic template R2 is selected from one or more of imidazole, 2-methylimidazole, 4-methylimidazole, 1-(3-aminopropyl)imidazole, 2-ethyl-4-methylimidazole, pyrrolidine, 1-(3-pyrrolidine)pyrrolidine, N-ethyl-2-aminomethylpyrrolidine; the solvent S1 is selected from one or more of N,N-dimethylformamide, N,N-dimethylacetamide, N,N-diethylformamide and N,N-dibutylformamide; the solvent S2 is selected from one or more of 1,4-dioxane, cyclohexane, cyclohexanone and cyclohexanol; and/or the solvent S3 is selected from one or more of methanol, ethanol, ethylene glycol, butanol and water.

Further, the organic template R1 is preferably one or more of tetraethylammonium bromide, tetraethylammonium hydroxide, tetrapropylammonium hydroxide and tetrabutylammonium hydroxide; the organic template R2 is preferably one or more of 1-(3-aminopropyl) imidazole, 2-ethyl-4-methylimidazole, N-ethyl-2-aminomethylpyrrolidine; the solvent S1 is preferably one or two of N,N-dimethylacetamide and N,N-dibutylformamide; the solvent S2 is preferably one or two of 1,4-dioxane and cyclohexanone; and/or the solvent S3 is preferably one or both of ethanol and water, wherein water is preferably deionized water.

Further, in the mixture, the molar constitution of the aluminum source based on Al$_2$O$_3$, the silicon source based on SiO$_2$, the phosphorus source based on P$_2$O$_5$, the organic templates R1+R2, the solvents S1+S2+S3 is as follows: SiO$_2$/Al$_2$O$_3$=0-1, preferably 0.1-0.75; P$_2$O$_5$/Al$_2$O$_3$=0.5-2, preferably 0.75-1.5; templates R1+R2/Al$_2$O$_3$=1-200, preferably 5-50; solvents S1+S2+S3/Al$_2$O$_3$=5-500, preferably 35-120.

Further, the molar ratio of the organic template R1 to the organic template R2 is 0.01 to 1:1, preferably 0.1 to 0.25:1.

Further, the molar ratio of the solvent S1, the solvent S2 and the solvent S3 is 1:0.01-1:1-100, preferably 1:0.05-0.5:10-80.

Further, the aluminum source is selected from one or more of aluminum isopropoxide, aluminate, metaaluminate, aluminum salts, hydroxide of aluminum, oxide of aluminum and aluminum-containing minerals, preferably one or two of aluminate and metaaluminate; the silicon source is selected from one or more of organic silicon, amorphous silicon dioxide, silica sol, solid silicon oxide, silica gel, diatomite and water glass, preferably one or more of amorphous silicon dioxide, silica sol and solid silicon oxide; the phosphorus source is selected from at least one of phosphoric acid, ammonium monohydrogen phosphate and ammonium dihydrogen phosphate, preferably orthophosphoric acid.

Further, in the preparation method, stirring and precipitation treatments are carried out before the crystallization treatment. The stirring time is 0.5-5 hours, the precipitation time is 1-12 hours.

Further, the conditions of the crystallization treatment include: the crystallization temperature of 120-200° C., preferably 140-180° C., more preferably 140-160° C.; the crystallization time of 1-5 days, preferably 3-5 days, more preferably 4-5 days.

Further, after the crystallization treatment, conventional post-processing is carried out, for example the steps of filtering, washing and drying to obtain the molecular sieve; and optionally the step of calcining the obtained molecular sieve.

According to the third aspect of the present invention, a molecular sieve composition is provided, including the SCM-34 molecular sieve described in the aforementioned first aspect or the SCM-34 molecular sieve prepared according to the method described in the aforementioned second aspect, and a binder. For example, a method of preparing the molecular sieve composition comprises the following steps:
 a. subjecting the SCM-34 molecular sieve according to the present invention to ammonium exchange, calcination to obtain a hydrogen-type SCM-34 molecular sieve;
 b. weighing a certain amount of the hydrogen-type SCM-34 molecular sieve obtained in step a, uniformly mixing it with a certain amount of binder and a pore forming agent, then kneading and extruding with a certain amount of water and dilute nitric acid solution to obtain a columnar sample, upon drying at 80-120° C. and calcining at 500-650° C. in sequence, obtaining a catalyst sample, wherein, the pore forming agent is selected from at least one of *sesbania* powder, carboxymethyl cellulose and starch.

According to the fourth aspect of the present invention, a use of molecular sieve is provided, that is, the use of the SCM-34 molecular sieve described in the aforementioned first aspect, the SCM-34 molecular sieve prepared according to the method described in the aforementioned second aspect, or the SCM-34 molecular sieve composition described in the aforementioned third aspect for preparing a metal containing AFI type molecular sieve. The metal containing AFI type molecular sieve has a special acid distribution and a novel morphology and is suitable for the methanol-to-olefin reaction.

The metal element in the metal containing AFI type molecular sieve is an alkaline earth metal and/or a transition metal element, preferably selected from at least one metal element in the IIA, IIB, IIIB, IVB or VIIIB group, and is further preferably at least one of magnesium, zinc, lanthanum, titanium, cobalt. Based on the mass of the AFI type molecular sieve, the content of the metal element is preferably 0.01%-1.0%.

The metal containing AFI molecular sieve has a weak acid center, a medium-strong acid center and a strong acid center at the same time. The acid content distribution is as follows: the weak acid content accounting for 30%-50% of the total acid content, the medium-strong acid content accounting for 5%-20% of the total acid content, and the strong acid content accounting for 30%-65% of the total acid content.

A method of preparing the metal containing AFI molecular sieve includes: using the SCM-34 molecular sieve according to the present invention as reactant raw material, mixing it with a solvent SI, an organic template R, a selectively added first silicon source to prepare a precursor A, and then mixing the precursor A with a solvent SII, a metal source, a selectively added second silicon source to prepare the AFI type molecular sieve.

Furthermore, based on the mass m of the fed SCM-34 molecular sieve, the mass ratio of raw materials used is: silicon source/m=0-20, organic template R/m=1-20, metal source/m=0.01-1, solvents (SI+SII)/m=2-100; preferably, silicon source/m=0.1-10, organic template R/m=2-10, metal source/m=0.05-0.5, solvents (SI+SII)/m=10-50; more preferably: silicon source/m=0.5-1, organic template R/m=3-6, metal source/m=0.1-0.25, solvents (SI+SII)/m=20-40.

Furthermore, the mass ratio of solvent SI to solvent SII is 0.1 to 20:1.

Further, the preparation method of the AFI type molecular sieve specifically includes the following steps:
 a. adding a SCM-34 molecular sieve, an organic template R to a solvent SI, selectively adding the first silicon source, stirring and carrying out a heat treatment to obtain a precursor A;
 b. mixing a metal source with a solvent SII, and selectively adding the second silicon source to obtain a mixture B;
 c. adding the precursor A to the mixture B while stirring to form a mixture to be crystallized;
 d. placing the mixture to be crystallized in step c under the condition of 60-100° C. and continuing the stirring for 0.5-2 hours for a crystallization reaction to obtain an AFI type molecular sieve.

Further, the organic template R is an organic amine, which is preferably selected from at least one of tetraethylammonium bromide, tetraethylammonium hydroxide, tetrapropylammonium bromide, tetrapropylammonium hydroxide, tetrabutylammonium bromide, tetrabutylammonium hydroxide, benzyltriethylammonium chloride, benzyltrimethylammonium hydroxide, triethylamine, n-butylamine, di-n-propylamine, diisopropylamine, ethylenediamine and ethylamine, further preferably at least one of tetraethylammonium hydroxide, benzyltrimethylammonium hydroxide and triethylamine.

Further, the solvent SI or the solvent SII is each independently selected from at least one of N,N-dimethylformamide, N,N-dimethylacetamide, ethylene glycol, ethanol and water, preferably at least one of N,N-dimethylformamide, ethanol and water.

Further, the first silicon source or the second silicon source is each independently selected from at least one of organic silicon, amorphous silicon dioxide, silica sol and solid silicon oxide; preferably, at least one of amorphous silicon dioxide, silica sol and solid silicon oxide.

Further, the metal source is selected from at least one of nitrate, sulfate and acetate of the corresponding alkaline earth metal and/or transition metal element, preferably nitrate of the corresponding metal.

Further, in step a, the heat treatment condition is: 0.5-2 hours at 40-80° C.

Further, in step d, the crystallization reaction conditions are: 110-160° C., preferably 110-145° C., more preferably 120-135° C.; the reaction time range of 10-120 minutes, preferably 20-100 minutes, more preferably 30-90 minutes.

Further, in step d, the crystallization product can go through post-processing steps, such as filtering, washing, drying, calcining, etc., and conventional operating conditions in the art can be adopted for the post-processing steps.

Specifically for example, as the filtration, for example, the obtained product mixture can be subjected to a simple vacuum filtration. As the washing, for example deionized water and/or ethanol can be used for the washing. As the drying temperature, for example, 40-250° C., preferably 60-150° C. can be listed, and as the drying time, for example, 3-30 hours, preferably 5-20 hours can be listed. The drying can be carried out under atmospheric pressure or reduced pressure. The calcining can be carried out in any way commonly known in the art, for example, the calcining temperature is generally 300-800° C., preferably 400-650° C., while the calcining time is generally 1-12 hours, preferably 3-12 hours. In addition, the calcining is generally carried out in an oxygen containing atmosphere, such as air or oxygen atmosphere.

The metal containing AFI type molecular sieve can be used in the reaction of methanol-to-hydrocarbon. Furthermore, the reaction conditions for methanol-to-hydrocarbon are as follows: methanol as raw material, reaction temperature of 400-600° C., reaction pressure of 0.01-10 MPa, and methanol weight space velocity of 0.1-15 h$^{-1}$.

The preparation method of the AFI type molecular sieve according to the present invention allows a rapid crystallization at a lower temperature, for example, the lowest reaction temperature is 110° C., and the fastest reaction time is 10 minutes. The obtained AFI molecular sieve is suitable for the methanol-to-olefin reaction, and has achieved good technical effect.

According to the fifth aspect of the present invention, a use of molecular sieve is provided. The SCM-34 molecular sieve described in the aforementioned first aspect, the SCM-34 molecular sieve prepared according to the method described in the aforementioned second aspect, or the SCM-34 molecular sieve composition described in the aforementioned third aspect is used for preparing an SAPO-17 molecular sieve. The SAPO-17 molecular sieve prepared herein has an excellent performance for the use in the industrial production of methanol downstream products, the industrial production of syngas downstream products, and the hydrocarbon cracking.

In one embodiment, the preparation method of SAPO-17 molecular sieve includes the following steps:

1) mixing an organic template cR and a first organic solvent cS for a first heat treatment to obtain a precursor P;
2) mixing the SCM-34 molecular sieve according to the present invention, a selectively added silicon source with a second organic solvent cS for a second heat treatment to obtain a mixture material M;
3) mixing the precursor P obtained in step 1) with the mixture material M obtained in step 2) to form a mixture to be crystallized;
4) pretreating the mixture to be crystallized obtained in step 3), and then carrying out a crystallization reaction to obtain an SAPO-17 molecular sieve.

Further, in step 1), the organic template cR is at least one of 1,10-phenanthroline, 2,2-bipyridine, 4,4-bipyridine, piperazine, cyclohexylamine and pyridine; preferably at least one of piperazine, cyclohexylamine.

Further, in step 1) and step 2), the first organic solvent cS and the second organic solvent cS are each independently selected from at least one of tetrahydrofuran, 2-methyltetrahydrofuran, 1,2-epoxycyclopentane, 1,4-dioxane, cyclohexanone, cyclohexanol; preferably, at least one of 1,4-dioxane, cyclohexanone.

Furthermore, the mass ratio of the added SCM-34 molecular sieve, the organic template cR and all the organic solvents cS is 0.1-1: 1-10:1-10, wherein, all the organic solvents cS are the total amount of the first organic solvent cS in step 1) and the second organic solvent cS in step 2). The mass ratio of the first organic solvent cS in step 1) to the second organic solvent cS in step 2) is 1:0.1-1.

Further, in step 1), the temperature of the first heat treatment is 40-90° C., the time is 1-5 hours; preferably, the temperature of the first heat treatment is 55-75° C., the time is 2-4 hours.

Further, in step 2), the temperature of the second heat treatment is 40-90° C., the time is 1-5 hours; preferably, the temperature of the second heat treatment is 50-70° C., the time is 2-3 hours.

Further, in step 2), the mass ratio of the silicon source to the SCM-34 molecular sieve is 0 to 10:1, preferably 0.1 to 10:1.

Further, in step 2), the silicon source is at least one of organic silicon, amorphous silicon dioxide, silica sol, silica, silica gel, diatomite and water glass; preferably, at least one of amorphous silica, silica sol and silica.

Further, in step 3), the mixing is preferably adding the precursor P into the mixture material M while stirring, the stirring time is 0.5 to 5 hours, preferably 2.5 to 4 hours.

Further, in step 4), the pretreatment condition is stirring for 0.5 to 5 h at 80 to 110° C.

Further, in step 4), the conditions of the crystallization reaction are: crystallization for 1 to 8 hours at 115 to 140° C.

The SAPO-17 molecular sieve can be used in the reactions of methanol-to-hydrocarbon and syngas-to-olefin.

Furthermore, the reaction conditions for the methanol-to-hydrocarbon are as follows: methanol as raw material, reaction temperature of 400-600° C., reaction pressure of 0.01-10 MPa, methanol weight space velocity of 0.1-15 h$^{-1}$.

Further, the reaction conditions for the syngas-to-olefin are as follows: syngas as raw material, $H_2/CO=0.5-1:1$, reaction temperature of 200-400° C., reaction pressure of 0.1-10 MPa, syngas weight space velocity of 20-2000 h$^{-1}$.

When the SAPO-17 molecular sieve prepared according to the present invention is used to the reaction of methanol-to-hydrocarbon, within the set evaluation conditions, the methanol conversion rate is 100%, the single pass yields of ethylene and propylene are up to 84.5%, and the selectivity ratio (ethylene/propylene) is in the range of 2.5-3.0, the catalyst has good stability.

During the course of using the SAPO-17 molecular sieve prepared according to the present invention in the reaction of syngas-to-olefin, within the set evaluation conditions, the highest CO conversion rate is up to 51.7%, the highest $C_2$-$C_4$ olefin selectivity is up to 85.6%, the selectivity ratio (ethylene/propylene) is in the range of 2.5-3.0.

Compared with the prior art, the preparation of the SAPO-17 molecular sieve according to the method of the present invention involves a shorter crystallization time, can shorten the total synthesis time of SAPO-17 molecular sieve to a certain extent at the same time, and can be conducted at a lower temperature. The SAPO-17 molecular sieve prepared by the crystal transformation of the SCM-34 molecular sieve according to the present invention significantly improves the use performance of SAPO-17 molecular sieve. The SAPO-17 molecular sieve synthesized by this method shows an excellent performance during the use in the industrial production of methanol downstream products, the industrial production of syngas downstream products, and the cracking of hydrocarbons. For example, in the reaction of the methanol conversion to hydrocarbon, the total yields of ethylene and propylene are high, and the selectivity ratio (ethylene/propylene) is high. In the reaction of syngas-to-hydrocarbon, the selectivity of $C_2$-$C_4$ olefins is high, the selectivity ratio (ethylene/propylene) is high.

MODE OF CARRYING OUT THE INVENTION

In order to facilitate the understanding of the present invention, the following examples are listed in the present invention. However, those skilled in the art should understand that the examples only serve to assist the understanding of the present invention, and should not be regarded as a specific limitation to the present invention. The end points and any values of the ranges disclosed in the present invention are not limited to the precise ranges or values, and these ranges or values should be understood to include the values close to these ranges or values.

In the present invention, the structure of the molecular sieve is determined by X-ray diffraction pattern (XRD), and the X-ray diffraction pattern (XRD) of the molecular sieve is determined by X-ray powder diffractometer, with a Cu-Kα ray source, a Kα1 wavelength λ=1.5405980 Å, a Ni filter.

In the present invention, an X'Pert PRO X-ray powder diffractometer (XRD) manufactured by PANalytical B.V. is used, with a working voltage of 40 kV, a current of mA and a scanning range of 3.5-50°. The product morphology is photographed with S-4800 Field Emission Scanning Electron Microscope (Fe-SEM) manufactured by HITACHI of Japan.

It should be noted particularly that the two or more aspects (or embodiments) disclosed in the context of the present invention can be arbitrarily combined with each other, and the technical solutions (such as methods or systems) thus formed are a part of the original disclosure in the present description, and also fall within the scope of protection in the present description.

Unless otherwise specified, all percentages, parts, ratios, etc. mentioned in the present invention are based on weight, unless taking weight as a basis is not in accordance with the conventional understanding of those skilled in the art.

The raw materials involved in the specific embodiments of the present invention are as follows:

aluminum sulfate[$Al_2(SO_4)_3 \cdot 18H_2O$]: an industrial product containing $Al_2O_3$, 15.7 wt. %;

aluminum isopropoxide [$Al(iPr)_3$]: containing $Al_2O_3$, 24.9 wt. %;

aluminum nitrate [$Al(NO_3)_3 \cdot 9H_2O$]: containing $Al_2O_3$, 27.5 wt. %;

phosphoric acid (purity≥85 wt. %): containing $P_2O_5$, 72.3 wt. %, commercially available;

acidic silica sol (40 wt. % aqueous solution): containing $SiO_2$, 40 wt. %, commercially available;

silica: containing $SiO_2$, 99 wt. %;

magnesium nitrate [$Mg(NO_3)_2 \cdot 6H_2O$]: containing MgO, 15.6 wt. %;

cobalt nitrate [$Co(NO_3)_2 \cdot 6H_2O$]: containing CoO, 25.7 wt. %;

zinc nitrate [$Zn(NO_3)_2 \cdot 6H_2O$]: containing ZnO, 27.3 wt. %.

I. Preparation of SCM-34 Molecular Sieve

Example 1

Figure 1:
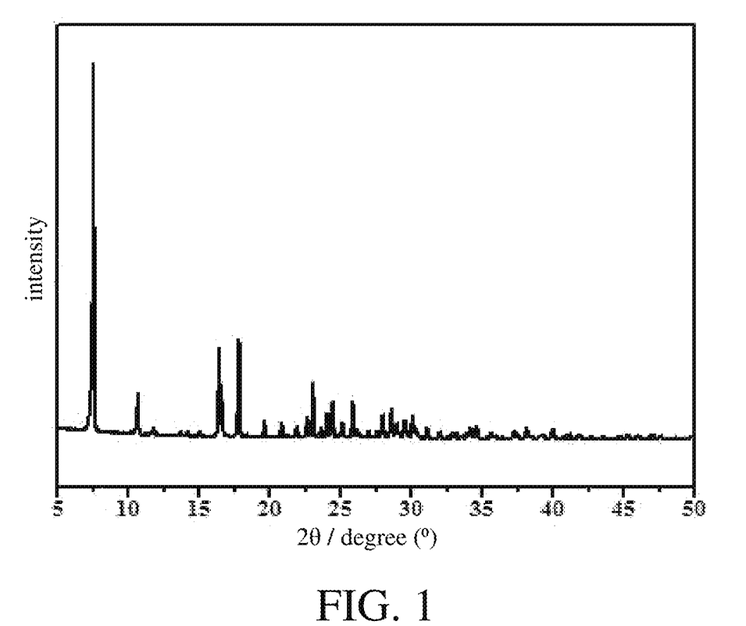
FIG. 1 is the X-ray diffraction (XRD) pattern of the molecular sieve prepared in Example 1.
Figure 2:
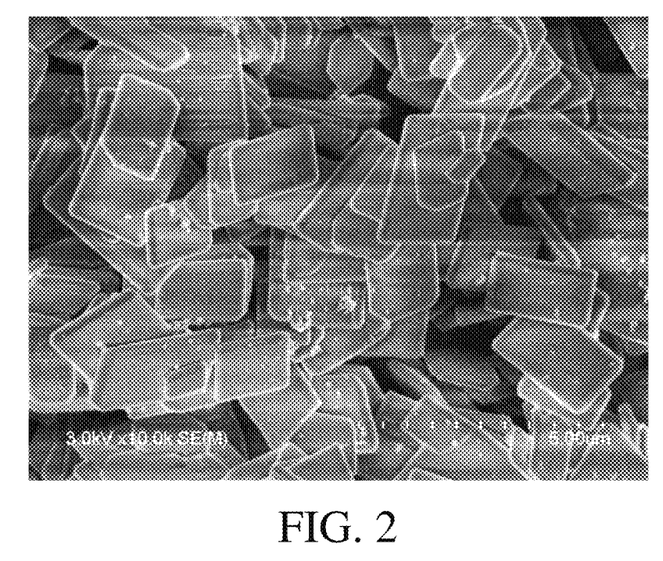
FIG. 2 is the SEM photo of the molecular sieve prepared in Example 1.

3.8 g of aluminum nitrate [$Al(NO_3)_3 \cdot 9H_2O$] was dissolved in 4.3 mL of deionized water to form a solution C after mixing. 1.8 g of phosphoric acid (purity≥85 wt. %), 10.8 g of tetrabutylammonium hydroxide (40 wt. % aqueous solution, MkSeal) and 10.4 g of 1-(3-aminopropyl) imidazole were then added to the solution C to obtain a solution C' after stirring for 0.5 hours, precipitating for 12 hours. Then, 0.1 g of silica (Aladdin, S104573, ≥99%), 1.4 mL of N,N-dibutylformamide and 0.4 mL of cyclohexanone were slowly added to the solution C' to form a uniform mixture to be crystallized after stirring for 3.5 hours and then subjecting to a heat treatment at 90° C. for 8 hours, wherein the molar ratio of aluminum source based on $Al_2O_3$, silicon source based on $SiO_2$, phosphorus source based on $P_2O_5$, total template and total solvent is: $Al_2O_3$:$SiO_2$:$P_2O_5$:template R:solvent S=1:0.1:1.5:5:35, template R1 (tetrabutylammonium hydroxide)/template R2 (1-(3-aminopropyl) imidazole)=0.2, solvent S1 (N,N-dibutyl formamide)/solvent S2 (cyclohexanone)/solvent S3 (water)=1:0.5:78.5. The above mixture to be crystallized was placed at 140° C. for crystallization for 5 days. After filtering, washing, the product was dried at 100° C. for 8 hours to obtain a product SCM-34. The X-ray diffraction pattern data are shown in Table 1, the X-ray diffraction pattern is shown in FIG. 1, and the SEM is shown in FIG. 2.

TABLE 1

| 2θ (°) | relative intensity, [($I/I_0$) × 100] |
|---|---|
| 7.39 | 100 |
| 10.24 | 16 |
| 10.71 | 35 |
| 12.01 | 6 |
| 14.20 | 5 |
| 16.44 | 32 |
| 17.93 | 35 |
| 19.71 | 9 |
| 21.01 | 18 |
| 23.31 | 19 |
| 24.25 | 15 |
| 26.03 | 15 |
| 27.81 | 11 |
| 28.13 | 13 |
| 30.02 | 10 |
| 31.33 | 5 |
| 34.73 | 7 |
| 38.28 | 6 |

Example 2

20.4 g of aluminum isopropoxide ($Al(iPr)_3$) was dissolved in 207.2 mL of water to form a solution C after mixing. 8.6 g of phosphoric acid (purity≥85 wt. %), 294.8 g of tetrabutylammonium hydroxide (40 wt. % aqueous solution, MkSeal) and 569.1 g of 1-(3-aminopropyl) imidazole were then added to the solution C to obtain a solution C' after stirring for 5 hours, precipitating for 1 hour. Then, 15.0 g of acidic silica sol (Ludox HS type, 40 wt. % aqueous solution), 313.2 mL of N,N-dimethylbutylamide and 9.8 mL of cyclohexanone were slowly added to the solution C' to form a uniform mixture to be crystallized after stirring for 2.5 hours and then subjecting to a heat treatment at 100° C. for 6 hours, wherein the molar ratio of aluminum source based on $Al_2O_3$, silicon source based on $SiO_2$, phosphorus source based on $P_2O_5$, total template and total solvent is: $Al_2O_3$:$SiO_2$:$P_2O_5$:template R:solvent S=1:0.5:0.75:25:120, template R1 (tetrabutylammonium hydroxide)/template R2 (1-(3-aminopropyl) imidazole)=0.1, solvent S1 (N,N-dimethylbutylamide)/solvent S2 (cyclohexanone)/solvent S3 (water)=1:0.05:11. The above mixture to be crystallized was placed at 140° C. for crystallization for 4 days. After filtering, washing, the product was dried at 120° C. for 4 hours to obtain a product SCM-34. The X-ray diffraction pattern data are shown in Table 2, and the XRD pattern is similar to FIG. 1.

TABLE 2

| $2\theta(°)$ | relative intensity, $[(I/I_0) \times 100]$ |
|---|---|
| 7.65 | 100 |
| 10.37 | 17 |
| 10.89 | 24 |
| 12.15 | 43 |
| 14.29 | 9 |
| 16.61 | 24 |
| 18.01 | 11 |
| 19.84 | 16 |
| 21.11 | 19 |
| 23.39 | 21 |
| 24.30 | 18 |
| 26.10 | 7 |
| 27.86 | 10 |
| 28.16 | 9 |
| 30.05 | 12 |
| 31.33 | 17 |
| 34.75 | 5 |
| 38.29 | 11 |

Example 3

1021.2 g of aluminum isopropoxide was dissolved in 1078.1 mL of water to form a solution C after mixing. 432.4 g of phosphoric acid (purity≥85 wt. %), 24016.3 g of tetraethylammonium hydroxide (40 wt. % aqueous solution, Sigma-Aldrich) and 54426.1 g of 1-(3-aminopropyl) imidazole were then added to the solution C obtain a solution C' after stirring for 3 hours, precipitating for 6 hours. Then, 450.0 g of silica (Aladdin, S104573, ≥99%), 4528.8 mL of N,N-dimethylbutylamine and 706.6 mL of cyclohexanone were slowly added to the solution C' to form a uniform mixture to be crystallized after stirring for 1.5 hours and then subjecting to a heat treatment at 90° C. for 11 hours, wherein the molar ratio of aluminum source based on $Al_2O_3$, silicon source based on $SiO_2$, phosphorus source based on $P_2O_5$, total template and total solvent is: $Al_2O_3$:$SiO_2$:$P_2O_5$:template R:solvent S=1:0.75:0.75:50:90, template R1 (tetraethylammonium hydroxide)/template R2 (1-(3-aminopropyl) imidazole)=0.15, solvent S1 (N, N-dimethylbutylamide)/solvent S2 (cyclohexanone)/solvent S3 (water)=1:0.25:30. The above mixture to be crystallized was placed at 140° C. for crystallization for 5 days. After filtering, washing, the product was dried at 90° C. for 10 hours to obtain a product SCM-34. The X-ray diffraction pattern data are shown in Table 3, and the XRD pattern is similar to FIG. 1.

TABLE 3

| $2\theta(°)$ | relative intensity, $[(I/I_0) \times 100]$ |
|---|---|
| 7.55 | 100 |
| 10.30 | 16 |
| 10.79 | 8 |
| 12.05 | 19 |
| 14.21 | 34 |
| 16.48 | 15 |
| 17.95 | 21 |
| 19.74 | 42 |
| 21.00 | 18 |
| 23.29 | 5 |
| 24.24 | 8 |
| 26.02 | 9 |
| 27.79 | 6 |
| 28.14 | 17 |
| 30.01 | 11 |
| 31.32 | 6 |
| 34.74 | 9 |
| 38.28 | 6 |

Example 4

375.1 g of aluminum nitrate was dissolved in 405.1 mL of water to form a solution C after mixing. 138.4 g of phosphoric acid (purity≥85 wt. %), 2827.6 g of tetrabutylammonium hydroxide (40 wt. % aqueous solution, MkSeal) and 3209.7 g of 1-(3-aminopropyl) imidazole were then added to the solution C to obtain a solution C' after stirring for 2 hours, precipitating for 8 hours. Then, 36.1 g of silica (Aladdin, S104573, ≥99%), 299.1 mL of N, N-dimethylformamide and 18.7 mL of cyclohexanone were slowly added to the solution C' to form a uniform mixture to be crystallized after stirring for 4 hours and then subjecting to a heat treatment at 110° C. for 3 hours, wherein the molar ratio of aluminum source based on $Al_2O_3$, silicon source based on $SiO_2$, phosphorus source based on $P_2O_5$, total template and total solvent is: $Al_2O_3$:$SiO_2$:$P_2O_5$:template R:solvent S=1:0.3:1.2:15:60, template R1 (tetrabutylammonium hydroxide)/template R2 (1-(3-aminopropyl) imidazole)=0.17, solvent S1 (N, N-dimethylbutylamide)/solvent S2 (cyclohexanone)/solvent S3 (water)=1:0.1:62. The above mixture to be crystallized was placed at 140° C. for crystallization for 5 days. After filtering, washing, the product was dried at 120° C. for 4 hours to obtain a product SCM-34. The X-ray diffraction pattern data are shown in Table 4, and the XRD pattern is similar to FIG. 1.

TABLE 4

| $2\theta(°)$ | relative intensity, $[(I/I_0) \times 100]$ |
|---|---|
| 7.75 | 100 |
| 10.41 | 11 |
| 10.90 | 8 |
| 12.15 | 17 |
| 14.39 | 32 |
| 16.60 | 22 |
| 18.05 | 13 |
| 19.84 | 17 |
| 21.09 | 10 |
| 23.38 | 23 |
| 24.31 | 21 |
| 26.08 | 14 |
| 27.85 | 11 |
| 28.16 | 19 |
| 30.03 | 22 |
| 31.33 | 9 |

TABLE 4-continued

| 2θ (°) | relative intensity, [(I/I₀) × 100] |
|---|---|
| 34.74 | 8 |
| 38.29 | 11 |

Example 5

33.3 g of aluminum sulfate [$Al_2(SO_4)_3 \cdot 18H_2O$] was dissolved in 66.3 mL of water to form a solution C after mixing. 5.2 g of phosphoric acid (purity≥85 wt. %), 117.0 g of tetrabutylammonium hydroxide (40 wt. % aqueous solution, MkSeal) and 102.6 g of 1-(3-aminopropyl) imidazole were then added to the solution C to obtain a solution C' after stirring for 3 hours, precipitating for 6 hours. Then, 6.1 g of acidic silica sol (Ludox HS type, 40 wt. % aqueous solution), 25.5 mL of N,N-dimethylbutylamine and 4.8 mL of cyclohexanone were slowly added to the C' solution to form a uniform mixture to be crystallized after stirring for 4.5 hours and then subjecting to a heat treatment at 80° C. for 12 hours, wherein the molar ratio of aluminum source based on $Al_2O_3$, silicon source based on $SiO_2$, phosphorus source based on $P_2O_5$, total template and total solvent is: $Al_2O_3$:$SiO_2$:$P_2O_5$:total template agent R:total solvent S=1:0.4:0.9:10:80, template agent R1 (tetrabutylammonium hydroxide)/template agent R2 (1-(3-aminopropyl) imidazole)=0.22, solvent S1 (N, N-dimethylbutylamide)/solvent S2 (cyclohexanone)/solvent S3 (water)=1:0.3:48. The above mixture to be crystallized was placed at 140° C. for crystallization for 5 days. After filtering, washing, the product was dried at 100° C. for 8 hours to obtain a product SCM-34. The X-ray diffraction pattern data are shown in Table 5, and the XRD pattern is similar to FIG. 1.

TABLE 5

| 2θ (°) | relative intensity, [(I/I₀) × 100] |
|---|---|
| 7.50 | 100 |
| 10.27 | 16 |
| 10.76 | 9 |
| 12.03 | 21 |
| 14.20 | 11 |
| 16.45 | 35 |
| 17.87 | 25 |
| 19.71 | 31 |
| 20.95 | 17 |
| 23.31 | 16 |
| 24.23 | 25 |
| 26.01 | 5 |
| 27.79 | 17 |
| 28.14 | 24 |
| 30.02 | 23 |
| 31.33 | 9 |
| 34.73 | 9 |
| 38.28 | 6 |

Example 6

266.6 g of aluminum sulfate was dissolved in 157.5 mL of water to form a solution C after mixing. 50.7 g of phosphoric acid (purity≥85 wt. %), 614.6 g of tetraethylammonium hydroxide (25 wt. % aqueous solution) and 801.3 g of N-ethyl-2-aminomethylpyrrolidine (purity 95%, Meryer) were then added to the solution C to form a solution C' after stirring for 4.5 hours and precipitating for 3.5 hours. Then, 18.1 g of acidic silica sol (Ludox HS type, 40 wt. % aqueous solution), 124.9 mL of N,N-dimethylformamide and 60.2 mL of 1,4-dioxane were slowly added to the solution C' to form a uniform mixture to be crystallized after stirring for 3.5 hours and then subjecting to a heat treatment at 80° C. for 12 hours, wherein the molar ratio of aluminum source based on $Al_2O_3$, silicon source based on $SiO_2$, phosphorus source based on $P_2O_5$, total template and total solvent is: $Al_2O_3$:$SiO_2$:$P_2O_5$:total template R:total solvent S=1:0.3:1.1:20:100, template R1 (tetraethylammonium hydroxide)/template R2 (N-ethyl-2-aminomethylpyrrolidine)=0.15, solvent S1 (N, N-dimethylbutylamine)/solvent S2 (1,4-dioxane)/solvent S3 (water)=1:0.4:22. The above mixture to be crystallized was placed at 140° C. for crystallization for 5 days. After filtering, washing, the product was dried at 100° C. for 8 hours to obtain a product SCM-34. The X-ray diffraction pattern data are shown in Table 6, and the XRD pattern is similar to FIG. 1.

TABLE 6

| 2θ (°) | relative intensity, [(I/I₀) × 100] |
|---|---|
| 7.50 | 100 |
| 10.27 | 16 |
| 10.76 | 17 |
| 12.03 | 27 |
| 14.20 | 13 |
| 16.45 | 23 |
| 17.87 | 14 |
| 19.71 | 41 |
| 20.95 | 15 |
| 23.31 | 10 |
| 24.23 | 33 |
| 26.01 | 6 |
| 27.79 | 7 |
| 28.14 | 14 |
| 30.02 | 28 |
| 31.33 | 7 |
| 34.73 | 8 |
| 38.28 | 9 |

II. Synthesis and Use of Metal Containing AFI Type Molecular Sieves

1. Synthesis of Metal Containing AFI Type Molecular Sieves from SCM-34 Molecular Sieve Example 7

Figure 3:
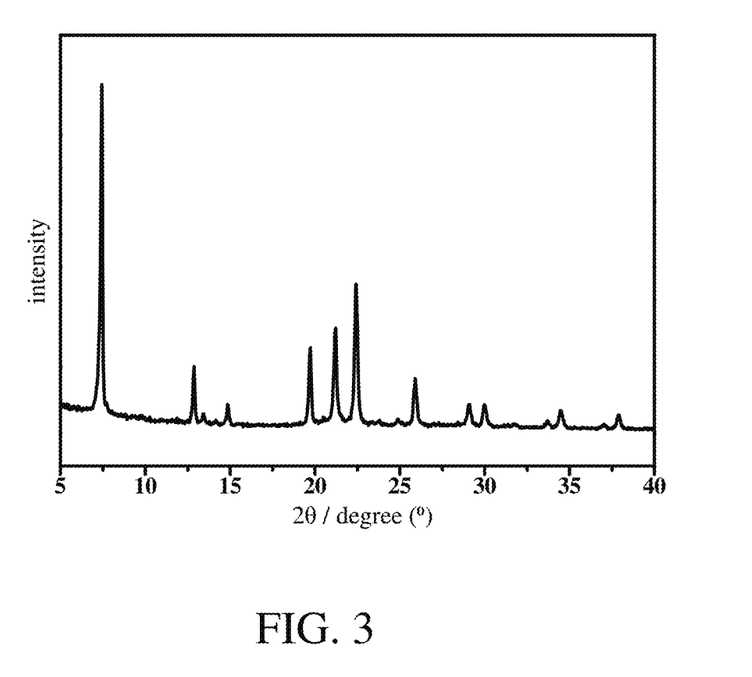
FIG. 3 is the XRD pattern of the AFI type molecular sieve synthesized in Example 9.
Figure 4:
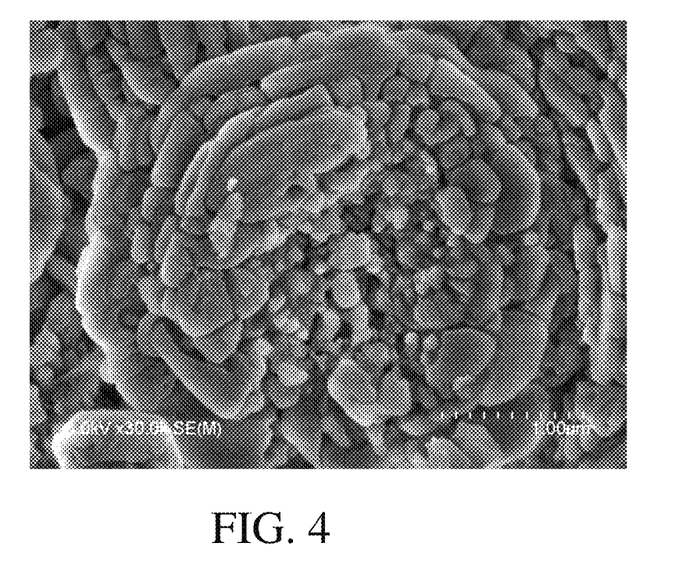
FIG. 4 and FIG. 5 are the SEM photos of the AFI type molecular sieve synthesized in Example 9.
Figure 5:
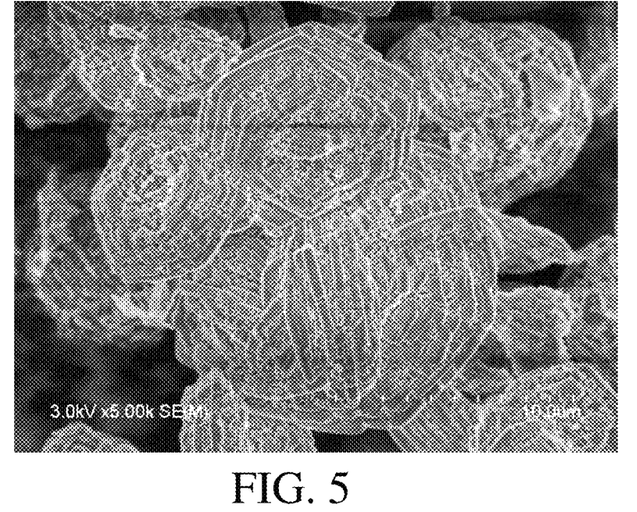

At room temperature, 136.2 g of the SCM-34 molecular sieve obtained in Example 1, 34.7 g of triethylamine[TEA], 237.6 g of tetraethylammonium bromide[TEABr] and 12008.3 g of deionized water were sufficiently stirred, and then placed at 80° C. for a heat treatment for 0.5 hours to obtain a precursor A. 1.4 g of magnesium nitrate [$Mg(NO_3)_2 \cdot 6H_2O$, purity≥98 wt. %] was dissolved in 1161.7 mL of deionized water to form a mixture B after stirring sufficiently for 1.5 hours. The precursor A was fed to the mixture B under a closed stirring condition, the stirring was continued for 3.5 hours and was further continued for 1 hour at 85° C. Then it was crystallized at 160° C. for 10 min, dried at 100° C. for 6 hours after filtering and washing, then heated to 600° C., calcined at a constant temperature for 4 hours, and thus an AFI molecular sieve (the same below) was obtained, marked as SSP5-1. Through ICP test, the SSP5-1 contains 0.18 wt. % Mg element. Its XRD pattern is similar to FIG. 3, SEM pattern is similar to FIG. 4 and FIG. 5, and the metal content and the acid distribution in the product are listed in Table 7.

Example 8

At room temperature, 20.8 g of the SCM-34 molecular sieve obtained in Example 2, 208 g of triethylamine [TEA], 4.2 g of silica [$SiO_2$, 99 wt. %] and 685.6 g of deionized water were stirred sufficiently, and then placed at 60° C. for a heat treatment for 1 hour to obtain a precursor A. 1.1 g of cobalt nitrate [$Co(NO_3)_2 \cdot 4H_2O$, purity≥99 wt. %], 6.3 g of silica [$SiO_2$, 99 wt. %] were dissolved in 354.4 mL of deionized water to form a mixture B after stirring sufficiently for 2.5 hours. The precursor A was fed into the mixture B under a closed stirring condition, the stirring was continued for 0.5 hours and was further continued for 0.5 hours at 100° C. under a closed state. The above mixture after stirring was then crystallized at 110° C. for 120 min, filtered, washed, and then dried at 90° C. for 8 hours, then heated to 500° C., calcined at a constant temperature for 8 hours to obtain a product, marked as SSP5-2. After ICP test, the SSP5-2 contains 0.01 wt. % Co element. Its XRD pattern is similar to FIG. 3, SEM pattern is similar to FIG. 4 and FIG. 5, and the metal content and the acid distribution in the product are listed in Table 7.

Example 9

Figure 6:
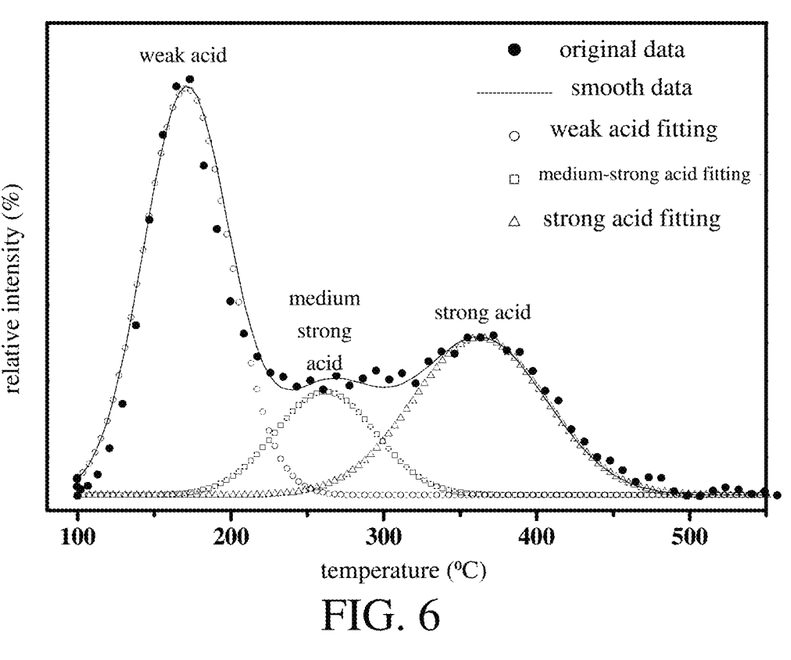
FIG. 6 shows the TPD pattern of the AFI type molecular sieve synthesized in Example 9.

At room temperature, 12110.7 g of the SCM-34 molecular sieve obtained from Example 4, 8106.3 g of benzyltriethylammonium chloride [TEBAC, 99 wt. %], 4004.4 g of tetraethylammonium hydroxide [TEAOH, 50%] and 15363.4 g of acidic silica sol [$SiO_2$, 40 wt. %] were sufficiently stirred for 1.5 hours, and then placed at 60° C. for a heat treatment for 1.5 hours to obtain a precursor A. 6055.4 g of zinc nitrate [$Zn(NO_3)_2 \cdot 6H_2O$, purity≥99 wt. %] and 15363.4 g of acidic silica sol [$SiO_2$, 40 wt. %] were dissolved in 4052.9 mL of deionized water to form a mixture B after stirring sufficiently for 2.5 hours. The precursor A was fed into the mixture B under a closed stirring condition, the stirring was continued for 0.5 hours, and further continued at 90° C. for 0.9 hours under a closed state. The above mixture after stirring was then crystallized at 115° C. for 86 min, filtered, washed, and then dried at 80° C. for 9 hours, then heated to 550° C., calcined at a constant temperature for 5 hours to obtain a product, marked as SSP5-3. Through ICP test, the SSP5-3 contains 1.0 wt. % Zn element. Its XRD pattern is FIG. 3, SEM pattern is FIG. 4 and FIG. 5, TPD pattern is FIG. 6, and the metal content and the acid distribution in the product are listed in Table 7.

TABLE 7

| sample name | type and weight content of metal element | weak acid (percentage in total acid) | medium-strong acid (percentage in total acid) | strong acid (percentage in total acid) |
|---|---|---|---|---|
| SSP5-1 | Mg, 0.18% | 42.8% | 5.0% | 52.2% |
| SSP5-2 | Co, 0.01% | 34.5% | 7.5% | 58.0% |
| SSP5-3 | Zn, 1.0% | 43.9% | 19.7% | 36.4% |

2. Use of Metal Containing AFI Type Molecular Sieves in the Reaction of the Methanol Conversion to Hydrocarbons

Example 10

The SSP5-1 molecular sieve synthesized in Example 7 was calcined at 550° C. for 4 hours, cooled to room temperature, then tableted, smashed and screened. 12-20 meshes of particles were selected for later use. Using methanol as raw material and a fixed bed reactor with a diameter of 15 mm, an assessment was carried out under the conditions of 505° C., a mass space velocity of 3.5 $h^{-1}$ and a pressure of 1.7 MPa. The yields of ethylene, propylene and butylene were up to 96.8%. Good technical results were obtained.

Example 11

The SSP5-2 molecular sieve synthesized in Example 8 was calcined at 550° C. for 4 hours, cooled to room temperature, then tableted, smashed and screened. 12-20 meshes of particles were selected for later use. Using methanol as raw material and a fixed bed reactor with a diameter of 15 mm, an assessment was carried out under the conditions of 400° C., a mass space velocity of 0.5 $h^{-1}$ and a pressure of 5.1 MPa. The yields of ethylene, propylene and butylene were up to 92.6% and good technical results were obtained.

Example 12

The SSP5-3 molecular sieve synthesized in Example 9 was calcined at 550° C. for 4 hours, cooled to room temperature, then tableted, smashed and screened. 12-20 meshes of particles were selected for later use. Using methanol as raw material and a fixed bed reactor with a diameter of 15 mm, an assessment was carried out under the conditions of 600° C., a mass space velocity of 0.1 $h^{-1}$ and a pressure of 0.01 MPa. The yields of ethylene, propylene and butylene were up to 90.9% and good technical results were obtained.

III. Synthesis and Use of SAPO-17 Molecular Sieve

1. Synthesis of SAPO-17 Molecular Sieve from SCM-34 Molecular Sieve

Example 13

Figure 7:
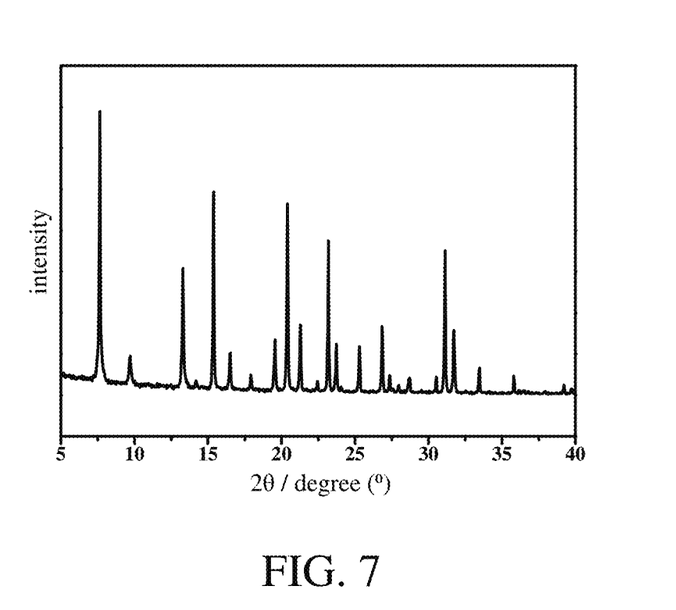
FIG. 7 is the XRD pattern of the SAPO-17 molecular sieve in Example 13.
Figure 8:
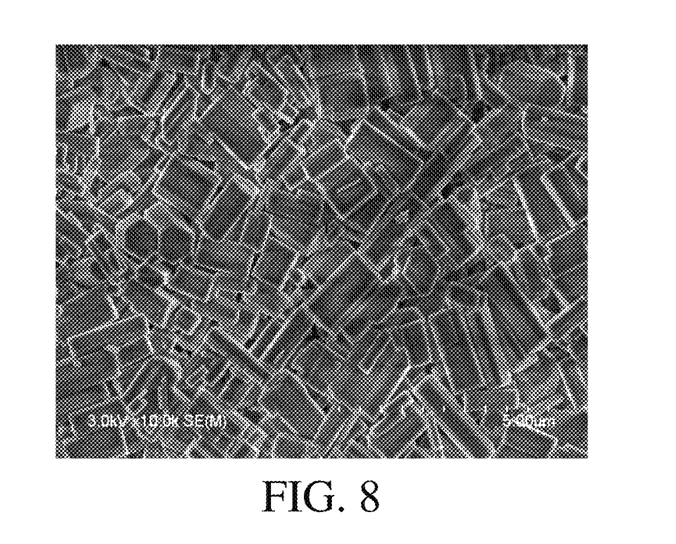
FIG. 8 is the SEM photo of the SAPO-17 molecular sieve in Example 13.

At room temperature, 2.6 g of piperazine (PIP) and 8.5 g of 1,4-dioxane (DOA) were sufficiently stirred, and then placed at 90° C. for a heat treatment for 1.0 hour to obtain a precursor $P_1$. 5.6 g of the SCM-34 molecular sieve prepared in Example 3 and 3.1 g of silica ($SiO_2$) were mixed in 6.9 g of 1,4-dioxane solution, and subjected to a heat treatment at 40° C. for 5 hours to obtain a mixture material $M_1$. The precursor $P_1$ was fed into the mixture material $M_1$ under the condition of vigorous stirring, and a mixture to be crystallized was formed after further stirring for 2.5 hours. The stirring was continued at 110° C. for 0.5 hours, and crystallization was then carried out at 140° C. for 1 hour. After filtering, washing, the product was dried at 120° C. for 4 hours, then heated to 500° C., and calcined at a constant temperature for 6 hours, and an SAPO-17 molecular sieve was obtained, marked as STE-1. See FIG. 7 for its XRD pattern and FIG. 8 for its SEM pattern.

Example 14

At room temperature, 666.7 g of 1,10-phenanthroline (1,10-PIH), 731.3 g of piperazine (PIP) and 1285.2 g of 1,2-epoxycyclopentane (CPO) were sufficiently stirred, and then placed at 40° C. for a heat treatment for 5 hours to obtain a precursor $P_2$. 239.8 g of the SCM-34 molecular sieve prepared in Example 5 was mixed in 139.8 g of 1,2-epoxycyclopentane (CPO) solution and subjected to a heat treatment at 90° C. for 1.0 hour to obtain a mixture material $M_2$. The precursor $P_2$ was fed into the mixture material $M_2$ under the condition of vigorous stirring. The stirring was continued for 4.0 hours, a closed stirring was then carried out at 80° C. for 5 hours, then crystallization was carried out at 130° C. for 2 hours. After filtering, washing, the product was dried at 100° C. for 6 hours, then heated to 600° C., and calcined at a constant temperature for 4 hours, and a product was obtained, marked as STE-2. Its XRD pattern is similar to FIG. 7, and its SEM pattern is similar to FIG. 8.

Example 15

At room temperature, 0.8 g of cyclohexylamine (HCHA), 33.7 g of piperazine (PIP), 5.5 g of 1,4-dioxane (DOA) and 5.2 g of cyclohexanone (CHO) were sufficiently stirred, and then placed at 55° C. for a heat treatment for 4.0 hours to obtain a precursor $P_3$. 6.9 g of the SCM-34 molecular sieve prepared in Example 6 was mixed in the solution of 5.0 g of 1,4-dioxane (DOA) and 5.7 g of cyclohexanone (CHO), and a heat treatment was carried out at 70° C. for 2.0 hours to obtain a mixture material $M_3$. The precursor $P_3$ was fed into the mixture material $M_3$ under the condition of vigorous stirring. The stirring was continued for 1 hour, a closed stirring was then carried out at 100° C. for 1 hour, and crystallization was then carried out at 120° C. for 5 hours. After filtering, washing, the product was dried at 80° C. for 9 hours, then heated to 400° C., and calcined at a constant temperature for 8 hours, and a product was obtained, marked as STE-3. Its XRD pattern is similar to FIG. 7, and its SEM pattern is similar to FIG. 8.

Comparative Example 1

Figure 9:
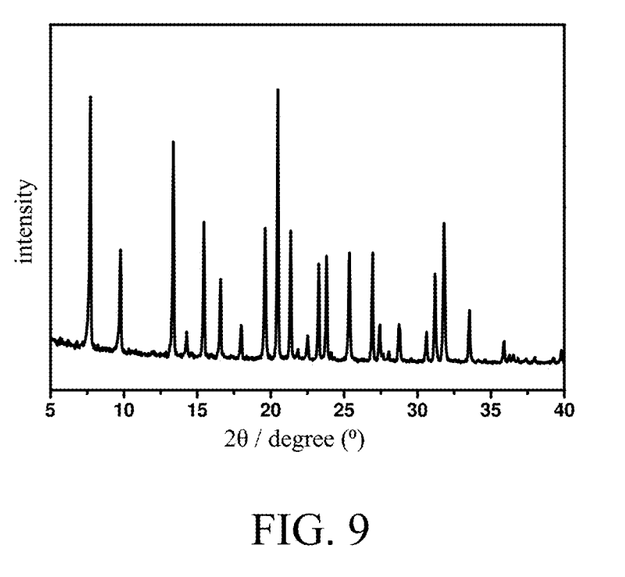
FIG. 9 is the XRD pattern of the SAPO-17 molecular sieve in Comparative Example 1.
Figure 10:
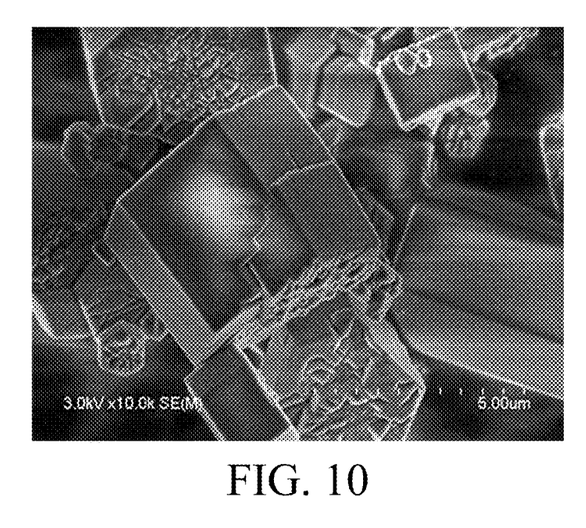
FIG. 10 shows the SEM photos of SAPO-17 molecular sieve in Comparative Example 1.

An SAPO-17 molecular sieve was prepared according to the synthesis method of SAPO-17 molecular sieve disclosed in CN103922361A, which is specifically as follows: with aluminum isopropoxide as aluminum source, phosphoric acid as phosphorus source, silica sol as silicon source, and cyclohexylamine as template, 81 g of aluminum isopropoxide was added to 48.9 g of ultrapure water, and 45.7 g of phosphoric acid (85 wt. %) was added after stirring evenly. After stirring for 1 hour, 11.5 mL of cyclohexylamine was added to the mixed solution, and after 2 hours of stirring and aging, 11.9 g of 30 wt. % $SiO_2$ aqueous solution was added to the system. After several hours of continuous aging, the sol was placed in a stainless steel reactor with a PTFE lining and crystallized at 200° C. for 120 hours to obtain a short and thick rod-like SAPO-17 molecular sieve. See FIG. 9 for its XRD pattern and FIG. 10 for its SEM pattern.

Comparative Example 2

According to a document (Tianjin Chemical Industry, 2016, 30 (3): 17-19), the synthesis method of SAPO-17 molecular sieve is specifically: with aluminum isopropoxide as aluminum source, phosphoric acid as phosphorus source, silica sol as silicon source, and cyclohexylamine as template, according to a solution of a reaction ratio of $1Al_2O_3$:$1P_2O_5$:$0.3SiO_2$:$1CHA$:$1HF$:$40H_2O$ and a fixed amount of aluminum source of 0.015 mol, 3.06 g of aluminum isopropoxide was added to 5.4 g of deionized water, 1.7 g of phosphoric acid (85 wt. %) was added after stirring evenly, 0.7 g of cyclohexylamine was added to the mixed solution after a continued stirring of 1.5 hours, 2.25 g of silica sol (40 wt. %) was added to the reaction system after stirring and aging for 1.5 hours, the sol was placed in a stainless steel reactor with a PTFE lining and crystallized at 200° C. for 120 hours to obtain an SAPO-17 molecular sieve after further stirring for several hours.

2. Use of SAPO-17 Molecular Sieve (1) Use of SAPO-17 Molecular Sieve in the Reaction of Methanol-to-Hydrocarbon Example 16

The STE-1 molecular sieve synthesized in Example 13 was calcined at 550° C. for 4 hours, cooled to room temperature, then tableted, smashed and sieved, and 12-20 meshes of particles were selected for later use. With methanol as raw material and a fixed bed reactor with a diameter of 15 mm, an assessment was conducted under the conditions of 600° C., a mass space velocity of 4.9 $h^{-1}$, and a pressure of 1.0 MPa. The methanol conversion rate was 100%, the yields of ethylene, propylene in the product were up to 78.7%, and the selectivity ratio (ethylene/propylene) was 2.87. Good technical results were obtained.

Example 17

The STE-2 molecular sieve synthesized in Example 14 was used to prepare a catalyst according to the catalyst preparation method in Example 16. Using methanol as raw material and a fixed bed reactor with a diameter of 15 mm, an assessment was carried out under the conditions of 550° C., a mass space velocity of 15 $h^{-1}$, and a pressure of 10 MPa. The methanol conversion rate was 100%, the yields of ethylene, propylene in the product were up to 80.8%, and the selectivity ratio (ethylene/propylene) was 2.76. Good technical results have been achieved.

Example 18

The STE-3 molecular sieve synthesized in Example 15 was used to prepare a catalyst according to the catalyst preparation method in Example 16. Using methanol as raw material and a fixed bed reactor with a diameter of 15 mm, an assessment was carried out under the conditions of 474° C., a mass space velocity of 7.1 $h^{-1}$, and a pressure of 2.4 MPa. The methanol conversion rate was 100%, the yields of ethylene, propylene in the product were up to 84.5%, and the selectivity ratio (ethylene/propylene) was 2.99. Good technical results have been achieved.

Comparative Example 3

The SAPO-17 molecular sieve synthesized in Comparative Example 1 was used to prepare a catalyst according to the catalyst preparation method of Example 16. By assessing according to the manner of Example 17, the methanol conversion rate was 100%, the yields of ethylene, propylene in the product were up to 33.3%, and the selectivity ratio (ethylene/propylene) was 1.1.

Comparative Example 4

The SAPO-17 molecular sieve synthesized in Comparative Example 2 was used to prepare a catalyst according to the catalyst preparation method of Example 16. By assessing according to the manner of Example 18, the methanol conversion rate was 100%, the yields of ethylene, propylene in the product were up to 40.1%, and the selectivity ratio (ethylene/propylene) was 1.2.

(2) Use of SAPO-17 Molecular Sieve in the Reaction of Syngas-to-Hydrocarbon

Example 19

Use of SAPO-17 Molecular Sieve in the Reaction of Syngas-to-Hydrocarbons

The STE-1 molecular sieve synthesized in Example 13 was calcined at 550° C. for 6 hours, then tableted, smashed, screened, and 20-40 meshes of particles were selected. A weight ratio of catalyst to filler $ZnCrO_x/STE=1.0$ ($ZnCrO_x$ represents a mixture of zinc oxide and chromium oxide, and an oxide-molecular sieve catalyst was prepared for later use) was used. With syngas as raw material and a fixed bed reactor with a diameter of 15 mm, the process conditions are: a reaction temperature of 400° C., a pressure of 10 MPa, a space velocity of 2000 $h^{-1}$, a syngas constitution $H_2/CO=0.5:1$, a CO conversion rate of 41.9%, wherein the $C_2$-$C_4$ olefin selectivity was 66.9%, and the selectivity ratio (ethylene/propylene)=2.61.

Example 20

Use of SAPO-17 Molecular Sieve in the Reaction of Syngas-to-Hydrocarbon

The STE-2 molecular sieve synthesized in Example 14 was used to prepare a catalyst according to the catalyst preparation method in Example 19. The process conditions are as follows: a reaction temperature of 375° C., a pressure of 7.5 MPa, a space velocity of 1000 $h^{-1}$, a syngas constitution $H_2/CO=0.66:1$, a CO conversion rate of 45.6%, wherein the $C_2$-$C_4$ olefin selectivity was 75.6%, and the selectivity ratio (ethylene/propylene)=2.66.

Example 21

Use of SAPO-17 Molecular Sieve in the Reaction of Syngas-to-Hydrocarbon

The STE-3 molecular sieve synthesized in Example 15 was used to prepare a catalyst according to the catalyst preparation method in Example 19. The process conditions are: a reaction temperature of 350° C., a pressure of 1.2 MPa, a space velocity of 500 $h^{-1}$, a syngas constitution $H_2/CO=0.75:1$, a CO conversion rate 51.7%, wherein the $C_2$-$C_4$ olefin selectivity was 85.6%, and the selectivity ratio (ethylene/propylene)=2.98.

Comparative Example 5

Use of SAPO-17 Molecular Sieve in the Reaction of Syngas-to-Hydrocarbon

The SAPO-17 molecular sieve synthesized in Comparative Example 2 was used to prepare a catalyst according to the catalyst preparation method of Example 20. By assessing according to the manner of Example 20, the CO conversion rate was 22.3%, wherein the $C_2$-$C_4$ olefin selectivity was 36.8%, and the selectivity ratio (ethylene/propylene) was 1.21.

It can be seen from the above comparative tests that the SAPO-17 molecular sieves prepared in the present invention have higher ethylene and propylene yields and higher selectivity ratios (ethylene/propylene) in the reaction of the methanol conversion to hydrocarbon; the SAPO-17 molecular sieves prepared in the present invention have higher $C_2$-$C_4$=selectivities and also higher selectivity ratios (ethylene/propylene) in the reaction of syngas-to-hydrocarbon.

The invention claimed is:

1. A SCM-34 molecular sieve, characterized in that the SCM-34 molecular sieve has a schematic chemical composition having a formula "$Al_2O_3$: $xSiO_2$: $yP_2O$", wherein $0 \leq x \leq 0.5$, $0.75 \leq y \leq 1.5$ and has an X-ray diffraction pattern including X-ray diffraction peaks as shown in the following table:

| 2θ (°) | relative intensity, $[(I/I_0) \times 100]$ |
|---|---|
| 7.59 ± 0.2 | 100 |
| 10.81 ± 0.1 | 5-50 |
| 16.52 ± 0.1 | 5-50 |
| 17.97 ± 0.1 | 5-50 |
| 23.34 ± 0.05 | 5-50 |
| 34.74 ± 0.05 | 5-50. |

2. The molecular sieve according to claim 1, characterized in that the X-ray diffraction pattern of the SCM-34 molecular sieve further includes X-ray diffraction peaks as shown in the following table:

| 2θ (°) | relative intensity, $[(I/I_0) \times 100]$ |
|---|---|
| 14.25 ± 0.1 | 5-50 |
| 21.01 ± 0.1 | 10-20 |
| 24.27 ± 0.05 | 5-50 |
| 26.05 ± 0.05 | 5-50 |
| 27.82 ± 0.05 | 5-50 |
| 28.15 ± 0.02 | 5-50 |
| 30.03 ± 0.02 | 5-50. |

3. The molecular sieve according to claim 1, characterized in that the X-ray diffraction pattern of the SCM-34 molecular sieve further includes X-ray diffraction peaks as shown in the following table:

| 2θ (°) | relative intensity, $[(I/I_0) \times 100]$ |
|---|---|
| 10.33 ± 0.1 | 10-20 |
| 12.09 ± 0.1 | 5-50 |
| 19.77 ± 0.1 | 5-50 |
| 31.33 ± 0.01 | 5-50 |
| 38.29 ± 0.01 | 5-50. |

4. A method of preparing the SCM-34 molecular sieve according to claim 1, comprising: crystallizing a mixture containing an aluminum source, a phosphorus source, an organic template R1, an organic template R2, a solvent S1, a solvent S2 and a solvent S3, and optionally a silicon source to obtain a crystallized mixture; and filtering, washing, and drying the crystallized mixture to obtain the SCM-34 molecular sieve;

wherein the organic template R1 is selected from one or more of quaternary ammonium salts and/or quaternary ammonium bases; the organic template R2 is selected from one or more of imidazole, pyrrolidine, and derivatives thereof; the solvent S1 is selected from one or more of amide group solvents; the solvent S2 is selected from one or more of the cyclic organic solvents; and the solvent S3 is selected from one or more of methanol, ethanol, ethylene glycol, butanol, and water, wherein the organic template R1 and the organic template R2 represent different organic templates from each other, and the solvent S1, the solvent S2 and the solvent S3 represent different solvents from each other.

5. The method according to claim 4, characterized in that the organic template R1 is selected from one or more of tetraethylammonium bromide, tetraethylammonium hydroxide, tetrapropylammonium bromide, tetrapropylammonium hydroxide, tetrabutylammonium bromide, tetrabutylammonium hydroxide; the organic template R2 is selected from one or more of imidazole, 2-methylimidazole, 4-methylimidazole, 1-(3-aminopropyl) imidazole, 2-ethyl-4-methylimidazole, pyrrolidine, 1-(3-pyrrolidine) pyrrolidine, N-ethyl-2-aminomethylpyrrolidine; the solvent S1 is selected from one or more of N, N-dimethylformamide, N, N-dimethylacetamide, N, N-diethylformamide and N, N-dibutylformamide; and/or the solvent S2 is selected from one or more of 1,4-dioxane, cyclohexane, cyclohexanone and cyclohexanol.

6. The method according to claim 4, characterized in that in the mixture, the molar constitution of the aluminum source based on $Al_2O_3$, the silicon source based on $SiO_2$, the phosphorus source based on $P_2O_5$, the organic templates R1+R2, and the solvents S1+S2+S3 is as follows: $SiO_2/Al_2O_3$-0-1; $P_2O_5/Al_2O_3$=0.5-2; templates $R1+R2/Al_2O_3$=1-200; and solvents $S1+S2+S3/Al_2O_3$=5-500.

7. The method according to claim 4, characterized in that the molar ratio of the organic template R1 to the organic template R2 is 0.01-1:1; and the molar ratio of the solvent S1, the solvent S2 and the solvent S3 is 1:0.01-1:1-100.

8. The method according to claim 4, characterized in that the crystallization of the mixture is conducted at a temperature of 120-200° C. and a crystallization time of 1-5 days.

9. A molecular sieve composition comprising the molecular sieve according to claim 1 and a binder.

10. A method of preparing a metal containing AFI molecular sieve includes:
  subjecting a mixture of the molecular sieve according to claim 1, a solvent SI, an organic template R, and an optional first silicon source to a heat treatment to prepare a precursor A;
  mixing a solvent SII, a metal source, and an optional second silicon source to prepare a precursor B;
  mixing the precursor A with the precursor B to form a mixture to be crystallized;
  crystallizing the mixture to be crystallized to obtain a crystallized mixture; and
  filtering, washing, drying, and calcining the crystallized mixture to obtain the AFI molecular sieve.

11. A method of preparing an SAPO-17 molecular sieve, including:
  1) subjecting a mixture of an organic template cR and a first organic solvent cS to a first heat treatment to obtain a precursor P;
  2) subjecting a mixture of the SCM-34 molecular sieve according to claim 1, an optional silicon source and a second organic solvent cS to a second heat treatment to obtain a mixture material M;
  3) mixing the precursor P with the mixture material M to form a mixture to be crystallized;
  4) pretreating the mixture to be crystallized obtained in step 3), and then carrying out a crystallization reaction to obtain a crystallized mixture; and
  5) filtering, washing, drying, and calcining the crystallized mixture to obtain the SAPO-17 molecular sieve.

12. A method for converting methanol to a hydrocarbon, comprising contacting the methanol with the SAPO-17 molecular sieve obtained by the method according to claim 11 under reaction conditions to obtain the hydrocarbon.

13. A method for converting syngas to a hydrocarbon, comprising contacting the syngas with the SAPO-17 molecular sieve obtained by the method according to claim 11 under reaction conditions to obtain the hydrocarbon.

* * * * *